US012758166B2

(12) United States Patent
Yang et al.

(10) Patent No.: US 12,758,166 B2
(45) Date of Patent: Oct. 13, 2026

(54) IMAGING SYSTEMS, METHODS, AND APPARATUS THEREOF

(71) Applicant: UNITED IMAGING HEALTHCARE NORTH AMERICA, INC., Houston, TX (US)

(72) Inventors: Dongxu Yang, Houston, TX (US); Xishan Sun, Houston, TX (US); Hongdi Li, Houston, TX (US); Xiaoying Wang, Shanghai (CN); Lingzhi Hu, Houston, TX (US)

(73) Assignee: UNITED IMAGING HEALTHCARE NORTH AMERICA, INC., Houston, TX (US)

( * ) Notice: Subject to any disclaimer, the term of this patent is extended or adjusted under 35 U.S.C. 154(b) by 0 days.

(21) Appl. No.: 18/638,641

(22) Filed: Apr. 17, 2024

(65) Prior Publication Data

US 2025/0325240 A1 Oct. 23, 2025

(51) Int. Cl.

| | |
|---|---|
| ***A61B 6/06*** | (2006.01) |
| ***A61B 6/58*** | (2024.01) |
| ***G01T 7/00*** | (2006.01) |
| ***G21K 1/02*** | (2006.01) |

(52) U.S. Cl.

CPC ................ *A61B 6/06* (2013.01); *A61B 6/585* (2013.01); *G01T 7/005* (2013.01); *G21K 1/025* (2013.01)

(58) Field of Classification Search

None

See application file for complete search history.

(56) References Cited

U.S. PATENT DOCUMENTS

| | | | | |
|---|---|---|---|---|
| 4,204,123 | A | 5/1980 | Stoddart | |
| 7,375,338 | B1 * | 5/2008 | Hugg | G21K 1/025 250/363.1 |
| 2016/0081635 | A1 * | 3/2016 | Divine | A61B 6/032 378/19 |
| 2017/0186507 | A1 * | 6/2017 | Kang | G21K 1/04 |
| 2020/0146641 | A1 * | 5/2020 | Mu | A61B 6/06 |

FOREIGN PATENT DOCUMENTS

| | | | |
|---|---|---|---|
| CN | 103226240 | A | 7/2013 |
| CN | 103385732 | A | 11/2013 |
| CN | 104382609 | B | 2/2017 |
| CN | 108472000 | A | 8/2018 |

(Continued)

*Primary Examiner* — Katherine L Fernandez

(74) *Attorney, Agent, or Firm* — METIS IP LLC

(57) ABSTRACT

The present disclosure provides an imaging system. The imaging system may include a detector including a detector including detecting modules arranged along the circumference direction of the imaging apparatus and configured to form the accommodation space; and a collimator including collimating modules arranged along the circumference direction and configured to rotate around the axis of the accommodation space that is perpendicular to the circumference direction. One of the collimating modules may include multiple collimating units in different configurations. The multiple collimating units may be arranged along the circumference direction. Each of the multiple collimating units may be switched between an effective state and an invalid state via a rotation of the collimator around the axis of the accommodation space.

16 Claims, 11 Drawing Sheets

(56) References Cited

FOREIGN PATENT DOCUMENTS

| | | | |
|---|---|---|---|
| CN | 105581806 | B | 7/2021 |
| CN | 114159084 | A | 3/2022 |
| CN | 116236217 | A | 6/2023 |
| CN | 116250855 | A | 6/2023 |
| WO | 2016012476 | A1 | 1/2016 |

* cited by examiner

IMAGING SYSTEMS, METHODS, AND APPARATUS THEREOF

TECHNICAL FIELD

The present disclosure relates to the field of medical imaging and, in particular, to imaging systems, methods, and apparatus thereof.

BACKGROUND

Single-photon emission computed tomography (SPECT) is a nuclear medicine imaging technique used to obtain images of organs or tissues of the human body through gamma rays produced by radioisotopes. In a SPECT system, a collimator may be used to collimate or shape a radiation field and define an incident angle of radiation rays reaching a detector, thereby ensuring that the acquired data by the detector is used to accurately reconstruct a distribution of a radiotracer inside a subject.

Therefore, the present disclosure provides an imaging system, an imaging method, and an imaging apparatus, and the imaging system includes a switchable collimator with multiple fields of view.

SUMMARY

According to one or more embodiments of the present disclosure, an imaging system is provided. The imaging system may include a detector including detecting modules arranged along a circumference direction of the imaging apparatus and configured to form the accommodation space. A gap may be involved between adjacent detecting modules among the detecting modules. The imaging system may also include a collimator including collimating modules arranged along the circumference direction and configured to rotate around an axis of the accommodation space that is perpendicular to the circumference direction. One of the collimating modules may include multiple collimating units in different configurations. The multiple collimating units may be arranged along the circumference direction, and each of the multiple collimating units may be switched between an effective state and an invalid state via a rotation of the collimator around the axis of the accommodation space.

In some embodiments, the multiple collimating units may be composed of a first portion and a second portion, and when the first portion of the multiple collimating units may be in the effective state, the second portion of the multiple collimating units may be in the invalid state.

In some embodiments, in the effective state, a projection of a first portion of the multiple collimating units along a radial direction on the detector may be located within the detecting module, and in the invalid state, a projection of a second portion of the multiple collimating units along the radial direction on the detector may be located within one or more gaps each of which may be between the detecting module and an adjacent detecting module.

In some embodiments, each of the collimating modules may correspond to one of the detecting modules, in the effective state, a radiation ray passing through the first portion of the multiple collimating units may be irradiated on the detecting module corresponding to the collimating module, in the invalid state, a radiation ray passing through one of the second portion of the multiple collimating units may be irradiated in one of the one or more gaps each of which may be between the detecting module and the adjacent detecting module.

In some embodiments, a projection, along the radial direction, of each of any two of the multiple collimating units on the detector may be independent.

In some embodiments, a length of the gap along the circumference direction may exceed a length of a collimating module along the circumference direction.

In some embodiments, the length of the gap along the circumference direction may exceed a length of the second portion of the multiple collimating units along the circumference direction.

In some embodiments, when the first portion of the multiple collimating units is in an edge region of the collimating module and in the effective state, the projection of the second portion of the multiple collimating units along the radial direction on the detector may be located within one single gap between the detecting module and the adjacent detecting module.

In some embodiments, when the first portion of the multiple collimating units is in a middle region of the collimating module and in the effective state, the second portion of the multiple collimating units may be in two edges region of the collimating module, the projection of the second portion of the multiple collimating units along the radial direction on the detector may be located within two gaps each of which may be between the detecting module and the adjacent detecting module.

In some embodiments, the collimator may include a notch, a projection of the notch along a radial direction may cover a detecting module, such that radiation rays passing through the notch may be irradiated on the detecting module.

In some embodiments, the notch may be used for calibration of each of the detecting modules by rotating the collimator to cause the projection of the notch along the radial direction to cover each of the detecting modules.

In some embodiments, when the first portion of the multiple collimating units is in the effective state, the collimator may be driven to rotate an angle based on a sampling rate of the imaging system.

In some embodiments, the imaging system may further include a rotation transmission apparatus configured to drive the collimator to rotate, the rotation transmission apparatus may include a rotating support and a driving component, the multiple collimating modules may be arranged on the rotating support, and the driving component may be configured to drive the rotating support to rotate.

In some embodiments, the rotation transmission apparatus may further include a positioning component configured to determine positions of the collimator modules.

In some embodiments, a configuration of a collimating unit may be defined by one or more structure parameters including at least one of an aperture of a hole in the collimating unit, a length of the hole, a taper angle of the hole, each of the multiple collimating units may correspond to one imaging requirement on one or more imaging parameters.

In some embodiments, the multiple collimating units may include a first collimating unit and a second collimating unit, the first collimating unit may correspond to a first field of view (FOV), and the second collimating unit may correspond to a second FOV that is different from the first FOV.

In some embodiments, the multiple collimating units may include a third collimating unit corresponding to a third FOV, and a center of the third FOV may be misalign with a center of a circumference plane where the third collimating unit is located.

According to one or more embodiments of the present disclosure, an imaging method is provided. The imaging method may include causing the collimator of the imaging apparatus to rotate around the axis of the imaging apparatus to cause a target collimating unit of the multiple collimating units in each collimating module of the collimator to be in the effective state; and causing the imaging apparatus to scan a subject to obtain scan data of the subject, wherein the imaging apparatus includes the detector including detecting modules arranged along the circumference direction of the imaging apparatus that is perpendicular to the axis of the imaging apparatus, a gap may be involved between adjacent detecting modules among the detecting modules; the collimating modules may be arranged along the circumference direction, and the multiple collimating units may be in different configurations.

In some embodiments, the collimator may include a notch, the imaging method may further include: causing the collimator to rotate around the axis of the imaging apparatus such that the notch of the collimator may correspond to a position of a detecting module; causing the imaging apparatus to scan a second subject to obtain the scan data of the second subject, at least a portion of the scan data may be generated by the detecting module; and calibrating the detecting module based on the scan data of the second subject.

According to one or more embodiments of the present disclosure, a collimator is provided. The collimator may include the multiple collimating modules arranged along the circumference direction of the collimator and configured to rotate around the axis that is perpendicular to the circumference direction, wherein one of the collimating modules may include the multiple collimating units in different configurations, the multiple collimating units may be arranged along the circumference direction, each of the multiple collimating units may be switched between the effective state and the invalid state via a rotation of the collimator around an axis of the collimator.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, where like reference numerals represent similar structures throughout the several views of the drawings, and wherein.

DETAILED DESCRIPTION

Figure 1:
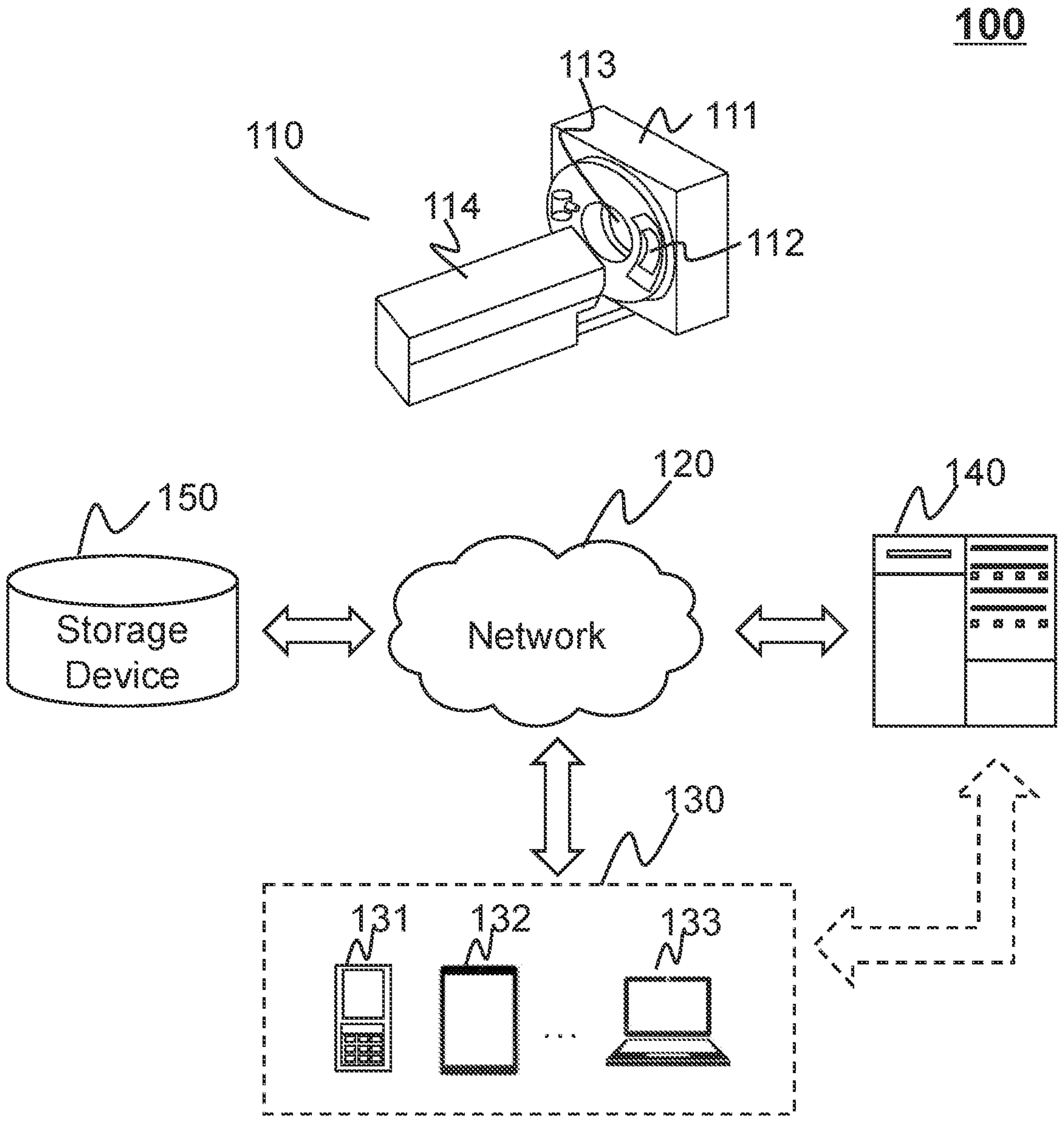
FIG. 1 is a schematic diagram illustrating an imaging system according to some embodiments of the present disclosure.

In order to illustrate the technical solutions related to the embodiments of the present disclosure, a brief introduction of the drawings referred to in the description of the embodiments is provided below. Obviously, the drawings described below are only some examples or embodiments of the present disclosure. Those skilled in the art, without further creative efforts, may apply the present disclosure to other similar scenarios according to these drawings. Unless apparent from the locale or otherwise stated, like reference numerals represent similar structures or operations throughout the several views of the drawings.

It should be understood that the term "system," "device," "unit," and/or "module" used herein are one method to distinguish different components, elements, parts, sections, or assemblies of different levels in ascending order. However, the terms may be displaced by another expression if they achieve the same purpose.

As used in the disclosure and the appended claims, the singular forms "a," "an," and/or "the" may include plural forms unless the content clearly indicates otherwise. In general, the terms "comprise," "comprises," and/or "comprising," "include," "includes," and/or "including," merely prompt to include steps and elements that have been clearly identified, and these steps and elements do not constitute an exclusive listing. The methods or devices may further include other steps or elements.

Unless otherwise defined, all technical and scientific terms used herein have the same meaning as commonly understood by those skilled in the art belonging to the present disclosure. The terms used herein in the specification of the present disclosure are for the purpose of describing specific embodiments only and are not intended to limit the invention. The term "and/or" as used herein includes any and all combinations of one or more of the relevant listed items.

A collimator may be used to collimate an emission direction of a gamma ray through one or more holes. An imaging apparatus may be used to perform scans for different fields of view (FOV) by changing different collimators in different configurations. However, a collimator may be made of a dense metallic material (such as lead or tungsten, etc.) and have a relatively large size and weight. Therefore, a replacement operation of the collimator from the imaging apparatus is complex, which needs an additional mechanical assistance and takes a long time. In addition, the replacement operation of the collimator is not able to be performed during scanning, such that a flexibility is relatively low. Further, the installing accuracy of different collimators is further ensured while replacing different collimators, which increases a complexity of the imaging apparatus and raises the production cost and maintenance difficulty of the imaging apparatus.

According to one or more embodiments of the present disclosure, an imaging system with a collimator is provided. The imaging system may include a detector including detecting modules arranged along a circumference direction of the imaging apparatus and configured to form the accommodation space. A gap may be involved between the adjacent detecting modules among the detecting modules. The imaging system may also include a collimator including collimating modules arranged along the circumference direction and configured to rotate around the axis of the accommodation space that is perpendicular to the circumference direction. One of the collimating modules may include multiple collimating units in different configurations. The multiple collimating units may be arranged along the circumference direction, and each of the multiple collimating units may be switched between an effective state and an invalid state via a rotation of the collimator around the axis of the accommodation space. Accordingly, the rotation of the collimator around the axis of the accommodation space may achieve the switching between different collimating units in different configurations, thereby satisfying different imaging requirements (e.g., different FOVs, different resolutions, different sensitivities, etc.)

FIG. 1 is a schematic diagram illustrating an exemplary imaging system according to some embodiments of the present disclosure.

As shown in FIG. 1, an imaging system 100 may include an imaging apparatus 110, a network 120, a terminal 130, a processing apparatus 140, and a storage apparatus 150.

The imaging apparatus 110 may be configured to scan a target object to obtain image data (e.g., projection data, images, etc.). In some embodiments, the imaging apparatus 110 may include a medical imaging apparatus, e.g., a single-photon emission computed tomography (SPECT) imaging apparatus, or other imaging apparatus, such as a computed tomography (CT) imaging apparatus, a positron emission tomography (PET), a SPET-CT imaging apparatus, a SPECT-MR imaging apparatus, and the like.

In some embodiments, the imaging apparatus 110 may include a gantry 111, a detector 112, and a scanning bed 114. A scanning region 113 may be provided for accommodating a subject to be scanned. The subject may be placed on the scanning bed 114 and moved into the scanning region 113 to be scanned. The gantry 111 may provide support for other components (e.g., the detector 112) of the imaging apparatus 110. In some embodiments, the detector 112 may include one or more detecting modules arranged along a circumference direction of the imaging apparatus and configured to form an accommodation space. The accommodation space may form the scanning region 113. A detecting module may include one or more detecting units arranged along a circumference direction perpendicular to an axial direction and/or the axial direction of the gantry 111. As used herein, the axial direction refers to a direction parallel to the long axis of the scanning bed 114. In some embodiments, each of the multiple detecting units may be configured to generate an electrical signal in response to detecting radiation rays. In some embodiments, each of the multiple detecting units or the detecting modules may be removable. It should be noted that the count of detecting modules in FIG. 1 is merely for illustration and not limit the scope of the present disclosure, and a count of detecting modules may be multiple. A detecting unit may include a scintillator (such as a cesium iodide detector), a semiconductor, or the like. In some embodiments, the imaging apparatus 110 may further include a collimator (not shown in the figure). The collimator may include multiple collimating modules arranged along the circumference direction of the imaging apparatus. Each of the multiple collimating modules may include multiple collimating units in different configurations. More descriptions of the collimator and/or detector may be found in different descriptions elsewhere in the present disclosure.

The network 120 may include any suitable network capable of facilitating an exchange of information and/or data for imaging apparatus 110. In some embodiments, at least one component of the imaging system 100 (e.g., the imaging apparatus 110, the terminal 130, the processing apparatus 140, the storage apparatus 150) may exchange the information and/or data with the at least one other component of the imaging system 100 through the network 120. For example, the processing apparatus 140 may obtain scan data from the imaging apparatus 110 through the network 120. In some embodiments, network 120 may include at least one network access point. For example, the network 120 may include a wired and/or wireless network access point (such as a base station and/or an Internet exchange point), and the at least one component of the imaging system 100 may be connected to the network 120 through the access point to exchange the data and/or information.

The terminal 130 may communicate and/or connect with the imaging apparatus 110, the processing apparatus 140, and/or the storage apparatus 150. In some embodiments, the terminal 130 may include a mobile apparatus 131, a tablet computer 132, a laptop computer 133, etc., or any combination thereof. For example, the mobile apparatus 131 may include a mobile control handle, a personal digital assistant (PDA), a smartphone, etc. or any combination thereof. In some embodiments, the terminal 130 may include a display apparatus, such as a monitor. The display apparatus may be configured to display images or other information obtained by imaging, such as a medical image of a patient, a three-dimensional model, or an operation panel related to medical imaging. In some embodiments, the terminal 130 may be a portion of the processing apparatus 140.

The processing apparatus 140 may be configured to the data and/or information obtained by the imaging apparatus 110, the terminal 130, the storage apparatus 150, or other components of the imaging system 100. For example, the processing apparatus may be configured to perform one or more operations of the imaging method (e.g., a method for calibration of the detector) disclosed in some embodiments of the present disclosure. In some embodiments, the processing apparatus 140 may include a single server or a server group. The server group may include a centralized server group or a distributed server group. In some embodiments, the processing apparatus 140 may include a local apparatus or a remote apparatus. For example, the processing apparatus 140 may access the information and/or data from the imaging apparatus 110, the storage apparatus 150, and/or the terminal 130 through the network 120. As another example, the processing apparatus 140 may be directly connected to the imaging apparatus 110, the terminal 130, and/or the storage apparatus 150 to access the information and/or data. As another example, the processing apparatus 140 may be installed on the imaging apparatus 110. In some embodiments, the processing apparatus 140 may be implemented on a cloud platform. For example, the cloud platform may include a private cloud, a public cloud, a hybrid cloud, a community cloud, a distributed cloud, an inter-cloud cloud, a multi-cloud, etc. or any combination thereof.

The storage apparatus 150 may be configured to store the data, instructions, and/or any other information. For example, the storage apparatus 150 may store the data obtained by the imaging apparatus 110, the terminal 130, and/or the processing apparatus 140. In some embodiments, the storage apparatus 150 may store the data and/or instructions used by the processing apparatus 140 to execute or use to accomplish an exemplary method described in the present disclosure. In some embodiments, the storage apparatus 150 may include a mass memory, a removable memory, a volatile read/write memory, a read-only memory (ROM), etc. or any combination thereof. In some embodiments, the storage apparatus 150 may be implemented on the cloud platform.

In some embodiments, the storage apparatus 150 may be connected to the network 120 to communicate with the at least one other component of the imaging system 100 (e.g., the processing apparatus 40, the terminal 130). The at least one component of the imaging system 100 may access the data stored in the storage apparatus 150 through the network 120. In some embodiments, the storage apparatus 150 may be a portion of the processing apparatus 140. In some embodiments, the processing apparatus 140 and the storage apparatus 150 may be integrated in the imaging apparatus 110.

It should be noted that the foregoing descriptions are merely provided for the purpose of illustration and are not intended to limit the scope of the present disclosure. For those skilled in the art, a variety of amendments and variations may be made under the teaching of the descriptions of the present disclosure. The features, structures, methods, and other characteristics of the exemplary embodiments described in the present disclosure may be combined in various manners to obtain additional and/or alternative exemplary embodiments. For example, the storage apparatus 150 may be a data storage apparatus that may include a cloud computing platform, such as public, private, community, and hybrid clouds. However, these amendments and variations do not depart from the scope of the present disclosure.

Figure 2:
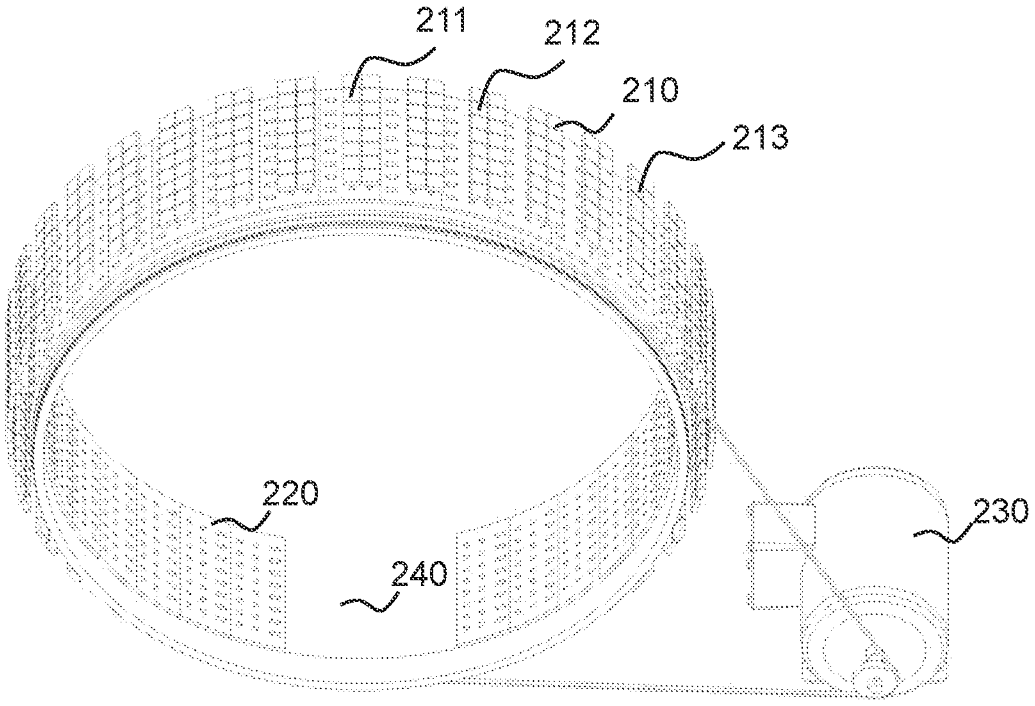
FIG. 2 is a schematic diagram illustrating an exemplary imaging apparatus according to some embodiments of the present disclosure.

FIG. 2 is a schematic diagram illustrating some exemplary components of an imaging apparatus according to some embodiments of the present disclosure. As shown in FIG. 2, the imaging apparatus may include a detector 210, a collimator 220, and a rotation transmission apparatus 230.

The detector 210 may be configured to detect radiation rays (e.g., gamma rays) emitted from a subject to be scanned. For example, after a radioactive tracer is injected into the subject, the radioactive tracer may decay to generate gamma rays. The gamma rays may be detected by the detector 210 and converted into electrical signals by the detector. The electrical signals may be further converted into digit signals which are used to generate an image of the subject.

In some embodiments, the detector 210 may include multiple detecting modules (e.g., a detecting module 211, a detecting module 212, and a detecting module 213, etc.) arranged along a circumference direction of the imaging apparatus to form an accommodation space. A gap may be involved between two adjacent detecting modules among the multiple detecting modules. In some embodiments, the length of the gap between the two adjacent detecting modules among the multiple detecting modules may be in a range of 2-4 cm. In some embodiments, the length of the gap between the two adjacent detecting modules among the multiple detecting modules may be in a range of 2-6 cm. In some embodiments, the length of the gap between the two adjacent detecting modules among the multiple detecting modules may be in a range of 2-8 cm. In some embodiments, the length of the gap between the two adjacent detecting modules among the multiple detecting modules may be in a range of 2-10 cm. In some embodiments, the length of the gap between the two adjacent detecting modules among the multiple detecting modules may be in a range of 2-15 cm. In some embodiments, the length of the gap between the two adjacent detecting modules among the multiple detecting modules may be in a range of 2-20 cm. As used herein, the length of the gap may refer to a distance between two close/neighbor edges of the two adjacent detecting modules along the circumference direction. The distance between two close edges of the two adjacent detecting modules along the circumference direction may be a straight-line distance, a minimum distance, a minimum arc length, etc., connecting the two close edges of the two adjacent detecting modules. It should be noted that the count of detecting modules in FIG. 2 is merely for illustration and not limit the scope of the present disclosure, and a count of detecting modules may be multiple.

In some embodiments, the multiple detecting modules may be arranged along the circumference direction to form a cylindrical structure.

In some embodiments, each of the multiple detecting modules may include multiple detecting units arranged along the circumference direction of the imaging apparatus and/or an axial direction perpendicular to the circumference direction. A detecting unit may be a basic unit of the detector for detecting radiation rays, and the detecting unit may refer to the smallest unit of the detector that may independently detect particles or radiation rays, and generate an electrical signal. The multiple detecting units may be packaged to form a detecting box, i.e., a detecting module. The detecting units in each detecting module may be arranged along the circumferential direction and/or the axial direction perpendicular to the circumferential direction.

In some embodiments, each of the multiple detecting modules may be detachable for efficiently adding, removing, and/or replacing the detecting modules from the imaging apparatus.

In some embodiments, each of the multiple detecting units may be detachable for efficiently adding, removing, and/or replacing the detecting units from the imaging apparatus.

Relative to an arrangement of a single detecting module along a certain position of the circumference direction, an arrangement of the multiple (two or more) detecting modules along the circumference direction may increase effective detecting areas of the detector. For example, the multiple detecting modules may work simultaneously to obtain data from different angles, thereby improving a resolution, enhancing a sensitivity, and improving a redundancy and reliability.

Figure 3A:
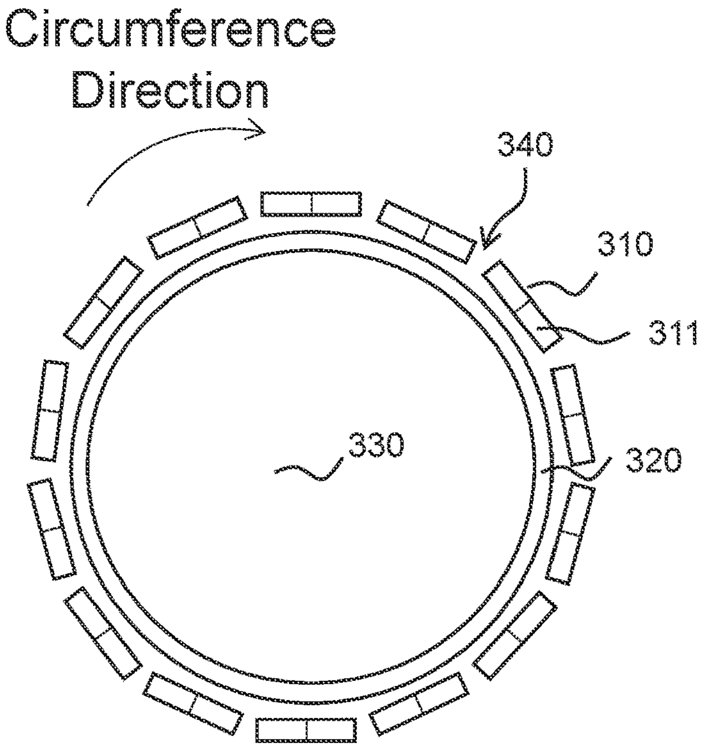
FIG. 3A is a schematic diagram illustrating an exemplary side view of a detector from the axial direction according to some embodiments of the present disclosure.

For example, FIG. 3A is a schematic diagram illustrating an exemplary side view of a detector from the axial direction according to some embodiments of the present disclosure. As shown in FIG. 3A, multiple detecting modules 310 may be arranged along the circumference direction denoted by the arrow in FIG. 3A. It should be noted that the count of detecting modules in FIG. 3A is merely for illustration and not limit the scope of the present disclosure, and a count of detecting modules may be multiple.

The circumference direction refers to a direction along an edge of a circle, for example, as shown by an arrow in FIG. 3A. The circumference direction of the imaging apparatus may be perpendicular to an axial direction of the imaging apparatus.

Figure 3B:
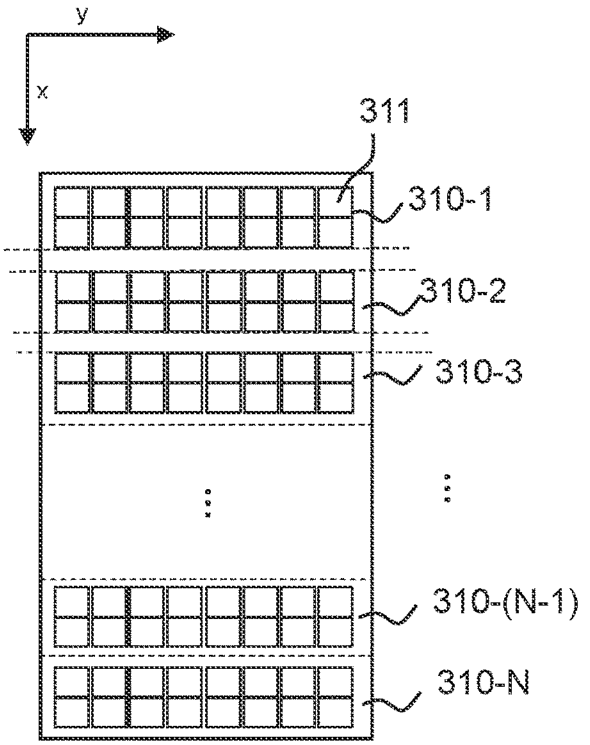
FIG. 3B is a schematic diagram illustrating an unfolding of a detector and a collimator along a circumference direction according to some embodiments of the present disclosure.

In some embodiments, the multiple detecting modules may be arranged at intervals. A space between adjacent detecting modules arranged at intervals may be a gap. For example, as shown in FIG. 3A, the space pointed to by an arrow 340 between two adjacent detecting modules in FIG. 3A may be the gap. As a further example, FIG. 3B is a schematic diagram illustrating an unfolding of a detector and a collimator 320 along a circumference direction according to some embodiments of the present disclosure. The X direction in FIG. 3B may correspond to the circumference direction in FIG. 3A, and the Y direction may correspond to the axial direction. As shown in FIG. 3A and FIG. B, multiple detecting modules 310-1, 310-2, 310-3 . . . 310-N may be arranged along the circumference direction. Each of the multiple detecting modules 310-1, 310-2, 310-3, . . . 310-(N−1), 310-N, may include multiple detecting units 311. The space between two adjacent detecting modules (e.g., the detecting modules 310-1 and 310-2) may be a gap between the two adjacent detecting modules (e.g., the detecting modules 310-1 and 310-2), such as the space defined by adjacent dotted lines as shown in FIG. 3B. It should be noted that the count of detecting modules in FIG. 3B is merely for illustration and not limit the scope of the present disclosure, and a count of detecting modules may be multiple.

In some embodiments, at least two of the multiple collimating units may correspond to one single gap. In other words, projections of the at least two of the multiple collimating units in the same collimating module along the radial direction of the accommodating space may be located with the single one gap, and radiation rays passing through the at least two of the multiple collimating units may reach the single one gap. The accommodation space surrounded by the detecting modules arranged along the circumference direction may provide a scanning region of the imaging apparatus. When a subject needs to be scanned, the subject may be located within the accommodation space to enable the detecting modules to detect radiation rays emitted from the subject.

In some embodiments, the accommodation space may be a cylindrical-like three-dimensional space, and the axial direction of the cylinder (i.e., the axial direction of the imaging apparatus) may be perpendicular to the circumference direction of the cylinder. As shown in FIG. 3A, the accommodation space 330 may be surrounded by the multiple detecting modules arranged along the circumference direction.

In some embodiments, the collimator 220 may include collimating modules arranged along the circumference direction and may be configured to rotate around an axis of the accommodation space that is perpendicular to the circumference direction.

The collimator is a component of the imaging system configured to constrain a transmission path of a ray. In some embodiments, the collimator may be made of a material with a relatively large attenuation coefficient for radiation rays (e.g., a dense metallic material such as lead, tungsten, uranium, etc.). In some embodiments, the collimator 220 and the detector 210 may be arranged concentrically. The collimator 220 may be arranged between the center of the accommodating space and the detector 210. Further, the collimator 220 may be closer to the detector 210 than the center of the accommodating space.

In some embodiments, the collimator may include multiple collimating modules arranged along the circumference direction of the detector, or the accommodating space, or the imaging apparatus.

In some embodiments, at least one of the multiple collimating modules may be detachable from the collimator 220 or the imaging apparatus 200. For example, the multiple collimating modules may be connected with a support of the collimator 220 via a detachable connection, such as a clamping connection, a screw connection, a rivet connection, a hinge connection, or the like, or a combination thereof. Via the detachable connection, one or more collimating modules may be detachable from the collimator or added to the collimator, thereby achieving the replacement of the one or more collimating modules.

In some embodiments, one of the collimating modules may include multiple collimating units. The multiple collimating units may be arranged along the circumference direction of the detector, or the accommodating space, or the imaging apparatus. A collimating unit may be a basic unit of the collimator. The multiple collimating units in a collimating module may be working independently. For example, when one of the multiple collimating units in the collimating module working or operating, others of the multiple collimating units in the collimating module may be not working. In some embodiments, the multiple collimating units in the collimating module may be packaged to form a collimating box, i.e., the collimating module. In some embodiments, the collimating box may include a shell for packing the multiple collimating units. The shell of the collimating box may be made of a material with a lower attenuation coefficient of the material of the collimating unit. For example, the shell if the collimating box may be made of a plastic, a rubber, a carbon fiber, or the like, or a combination thereof.

Each of the collimating units in a collimating module may include a main body and a set of holes arranged on the main body. The main body may include a material with a high attenuation coefficient. In some embodiments, different collimating units may include different main bodies. In some embodiments, the different main bodies corresponding to different collimating units may be an integrated body. The collimating module may include multiple sets of holes arranged on the integrated body. The set of holes may be configured to pass through radiation rays and define an incident direction of radiation rays passing through the set of holes. The set of holes may include through holes. Each of the sets of holes may include a hole canal. A radiation ray having an incident direction that is parallel to the extending direction of a hole canal may pass through the hole canal. A radiation ray whose incident direction is not parallel to the extending direction of the hole canal may be absorbed by the main body. Therefore, a collimating unit may define an incident direction of radiation rays passing through the set of holes in the collimating unit.

In some embodiments, according to the shapes of holes in a collimating unit, the collimating unit may include a set of pinholes, a set of parallel holes, a set of convergent holes, a set of fan-beam holes, etc. In some embodiments, the shape of the hole may include a circle, an oval, a polygon, and the like.

The collimating units in a collimating module may be in different configurations. As used herein, a configuration of a collimating unit may be defined by one or more structure parameters. The structure parameters of the collimating unit may include an aperture of a hole in the collimating unit, a hole spacing, a hole length, an opening angle, a count of the set of holes in the collimating unit, a distribution or arrangement of the set of holes in the collimating unit. The hole spacing refers to a distance between two adjacent holes in the collimating unit. The hole length refers to a length of a hole canal. For a pinhole, a fan-beam hole, or a convergent hole, the canal and/or the extension of a hole-like a cone, and the opening angle may also be referred to as a taper angle that is an angle between the two generatrixes of the axis section (passing through the axis of the cone) of the cone. The distribution or arrangement of the set of holes in the collimating unit may refer to positions of the set of holes in the collimating unit. For example, the set of holes in the collimating unit may be arranged in the main body of the collimating unit regularly, for example, in a form of a matrix including M row and N column. As another example, the set of holes in the collimating unit may be arranged in the main body of the collimating unit irregularly.

As used herein, different configurations of two collimating units may refer to that at least one of the one or more structure parameters of the two collimating units may be different. The same configuration of two collimating units may refer to that each of the one or more structure parameters of the two collimating units is the same.

In some embodiments, the structure parameters of the set of holes included in a same collimating unit may be the same (e.g., aperture, a hole spacing, a hole length, etc.).

Figure 4A:
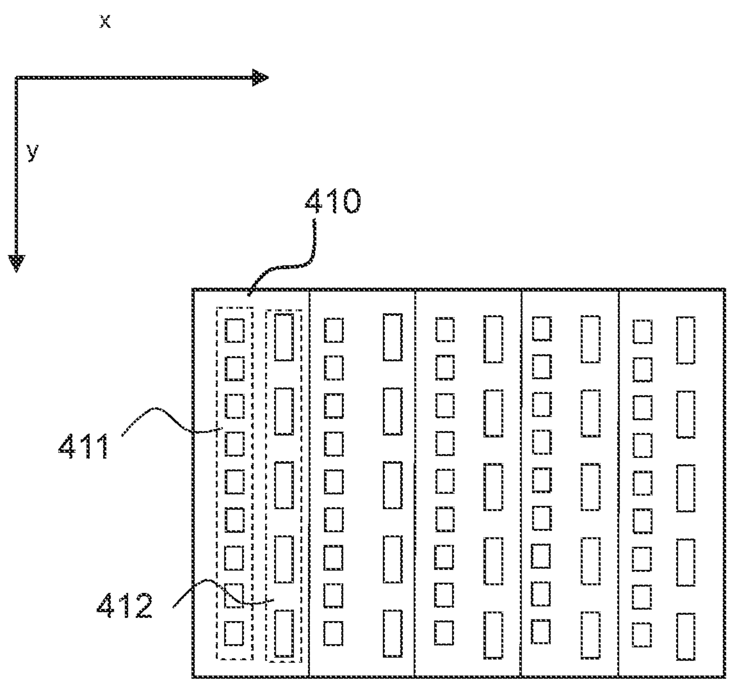
FIG. 4A is a schematic diagram illustrating exemplary collimating modules according to some embodiments of the present disclosure.
Figure 4B:
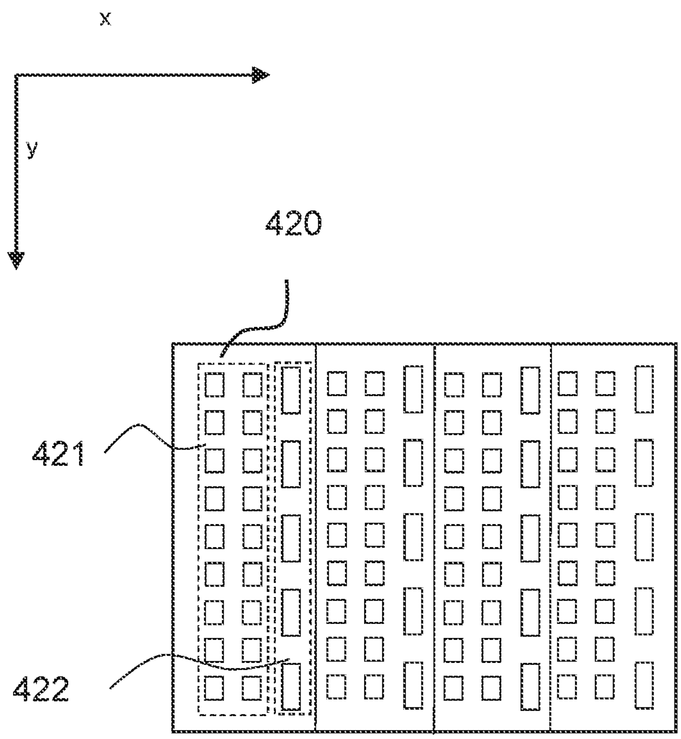
FIG. 4B is a schematic diagram illustrating exemplary collimating modules according to some embodiments of the present disclosure.

In some embodiments, the multiple collimating units in a collimating module may be arranged at intervals along the circumference direction (e.g., the x-direction as shown in FIG. 4A and FIG. 4B). Each of the collimating units may be provided with a set of holes having the same structure parameter (e.g., the aperture of the hole, the length of the hole, the opening angle of the hole, etc.) in an axial direction (e.g., y direction as shown in FIG. 4A and FIG. 4B) perpendicular to the circumference direction. In some embodiments, each of the collimating units may be provided with one or more than two columns of holes along the circumference direction, For example, FIG. 4A and FIG. 4B are schematic diagrams illustrating exemplary collimating modules according to some embodiments of the present disclosure. As shown in FIG. 4A and FIG. 4B, X direction represents the circumference direction, and the Y direction represents the axial direction of the accommodation space perpendicular to the circumference direction. As shown in FIG. 4A, multiple collimating modules may be arranged along the circumference direction. A collimating module 410 may include a collimating unit 411 and a collimating unit 412. The collimating unit 411 may include a set of holes each of which has a first aperture. The collimating unit 412 may include a set of holes each of which has a second aperture. The second aperture may be greater than the first aperture, such that the first collimating unit 411 and the second collimating unit 412 may have different configurations. The set of holes in the collimating unit 411 may be arranged in one row along the axial direction and the set of holes in the collimating unit 412 may be arranged in one row along the axial direction. As shown in FIG. 4B, a collimating module 420 may include a collimating unit 421 and a collimating unit 422. The collimating unit 421 may include a set of holes each of which has a first aperture. The collimating unit 422 may include a set of holes each of which has a second aperture. The second aperture may be greater than the first aperture, such that the first collimating unit 421 and the second collimating unit 422 may have different configurations. The set of holes in the collimating unit 421 may be arranged in two rows and the set of holes in the collimating unit 422 may be arranged in one row. It should be noted that the count of detecting modules in FIG. 4A and FIG. 4B is merely for illustration and not limit the scope of the present disclosure, and a count of detecting modules may be multiple.

In some embodiments, the multiple collimating modules may be rotated around an axis of the accommodation space perpendicular to the circumference direction to change the positions of the multiple collimating modules along the circumference direction. Each of the multiple collimating units may be switched between an effective state and an invalid state via a rotation of the collimator around the axis of the accommodation space.

In some embodiments, the multiple collimating modules may be rotated around the axis of the accommodation space with the rotation of the collimator 220 synchronously. In other words, when the collimator 220 rotates around the axis of the accommodation space, the multiple collimating modules may rotate synchronously around the axis of the accommodation space. In some embodiments, the multiple collimating modules may rotate around the axis of the accommodation space independently. For example, when one of the multiple collimating modules may rotate around the axis of the accommodation space and the other one of the multiple collimating modules may not rotate. In some embodiments, the multiple collimating modules may be rotated around the axis of the accommodation space through the rotation transmission apparatus 230. More descriptions for the rotation transmission apparatus 230 may be found elsewhere in the present disclosure.

Figure 5:
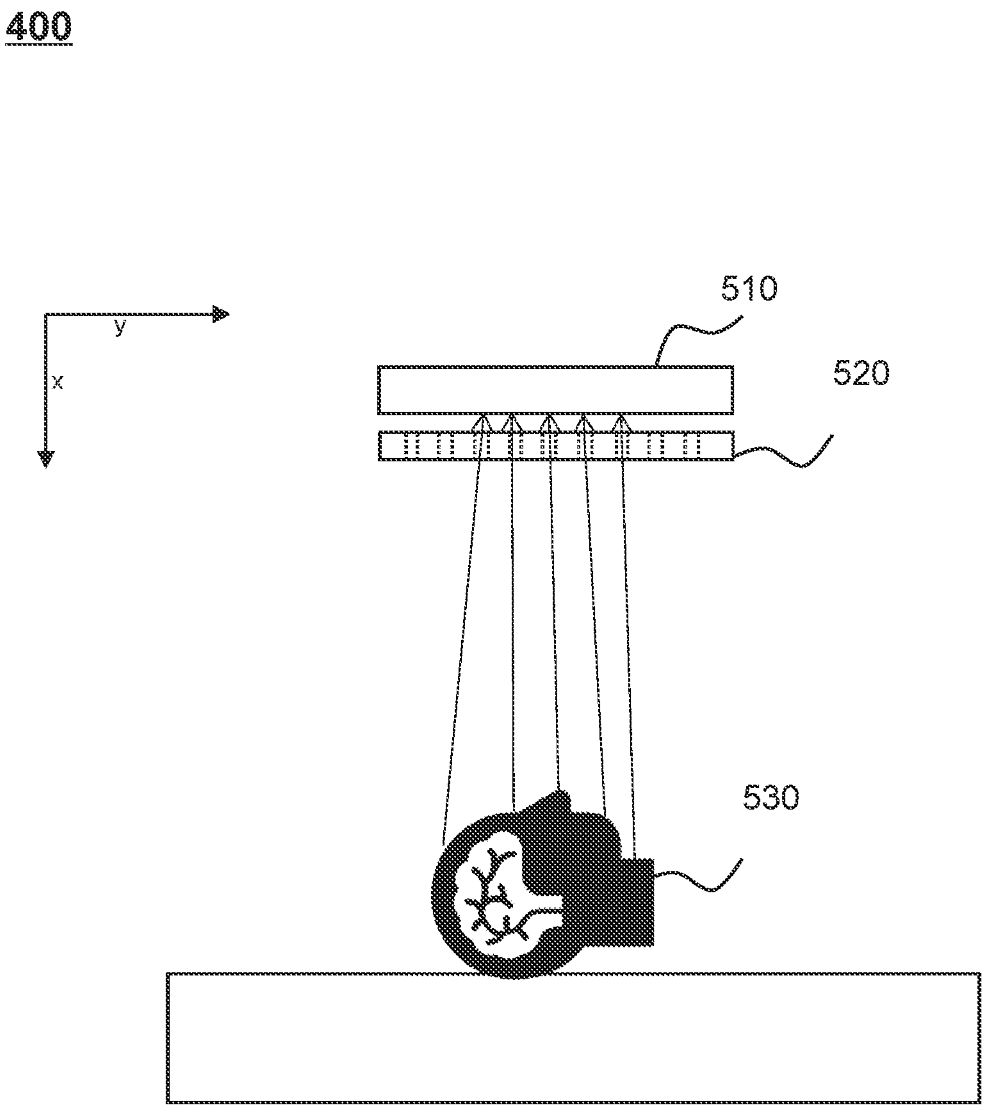
FIG. 5 is a schematic diagram illustrating an exemplary reception of radiation rays by detecting modules illustrating according to some embodiments of the present disclosure.

When a collimating unit may be in the effective state, a radiation ray passing through the collimating unit may be able to be received by a detecting module. The effective state may also be referred to as an operating state or working state. As shown in FIG. 5, a subject 530 may be located within the accommodation space. When the radiation rays emitted from the subject are able to pass through the set of holes in a collimating unit 520 to reach a detecting module 510, the collimating unit 520 may be in the effective state. It should be noted that the count of detecting modules in FIG. 5 is merely for illustration and not limit the scope of the present disclosure, and a count of detecting modules may be multiple.

When a collimating unit is in the invalid state, a radiation ray passing through the collimating unit may be not able to be received by a detecting module.

The rotation of a collimating module around the axis of the accommodation space may change the positions of the multiple collimating units in the collimating module along the circumference direction. When a collimating unit is rotated around the axis of the accommodation space to a position corresponding to a gap between two adjacent detecting modules, the radiation ray passing through the collimating unit may not be able be detected by a detecting module, thus the collimating unit may be in the invalid state. When the collimating unit is rotated around the axis of the accommodation space to a position corresponding to the detecting module, a radiation ray passing through the collimating unit may reach and be detected by the detecting module, thus the collimating unit may be in the effective state. As described herein, the position of a collimating unit corresponding to the position of a detecting module may refer to that a projection of the collimating unit along the radial direction of the accommodating space on a plane (e.g., the circumferential surface where in the detector is located) may be located within a projection of the detecting module on the plane along the radial direction of the accommodating space. The position of a collimating unit corresponding to the position of a gap between two adjacent detecting modules may refer to that a projection of the collimating unit along the radial direction of the accommodating space on a plane (e.g., the circumferential surface where in the detector is located) may be located within a projection of the gap between two adjacent detecting modules on the plane along the radial direction of the accommodating space.

Figure 6A:
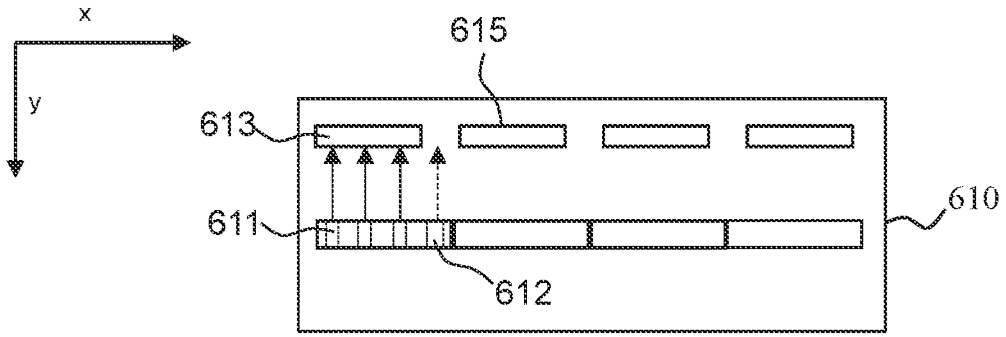
FIG. 6A is a schematic diagram illustrating an exemplary state of collimating units according to some embodiments of the present disclosure.
Figure 6B:
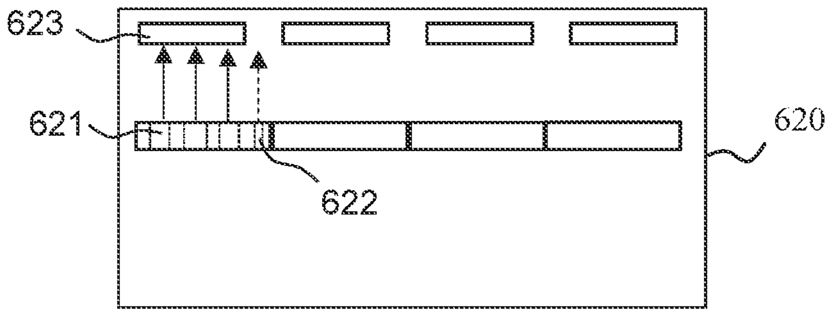
FIG. 6B is a schematic diagram illustrating an exemplary state of collimating units according to some embodiments of the present disclosure.

For example, FIG. 6A-6D are schematic diagrams illustrating exemplary states of collimating units according to some embodiments of the present disclosure. As shown in FIG. 6A-FIG. 6D, a side view of an imaging system corresponding to a detector and a top view of an imaging system corresponding to a collimator are shown, and the illustration is merely provided for a correspondence between exemplary radiation rays and holes of detecting modules and collimation modules. As shown in FIG. 6A, a collimating unit 611 may be in the effective state and the radiation rays passing through the collimating unit 611 may reach and be detected by a detecting module 613, and a collimating unit 612 may be in the invalid state and the radiation rays passing through the collimating unit 612 reach the gap between the two adjacent detecting modules 613 and 615 and may not be received by the detecting module 613 and the detecting module 615. The dotted lines in FIG. 6 may be used to delineate the collimating modules. It should be noted that the count of detecting modules in FIGS. 6A-6D is merely for illustration and not limit the scope of the present disclosure, and a count of detecting modules may be multiple.

In some embodiments, the multiple collimating units in a collimating unit may be composed of a first portion and a second portion. When the first portion of the multiple collimating units is in the effective state, the second portion of the multiple collimating units may be in the invalid state; when the first portion of the multiple collimating units is in the invalid state, the second portion of the multiple collimating units may be in the effective state.

For example, as shown in FIG. 6A, the collimating unit 611 in the effective state may be the first portion of the collimating units in a collimating module, and the collimating unit 612 in the invalid state may be one of the collimating units of the second portion.

In some embodiments, a collimating unit in the first portion and a collimating unit in the second portion may be changeable. For example, the collimating unit may be switched between the effective state and the invalid state by driving the collimating module to move along the circumference direction, and the collimating unit may be transformed in the first portion and the second portion according to the switching between the effective state and the invalid state. By driving the collimating module to rotate along the circumference direction (x-direction in FIG. 6), the position of the collimating unit may be changed, thereby causing the collimating unit to switch between the effective state and the invalid state. As a further example, when a collimating module is rotated by a certain angle, a collimating unit A in collimating module 1 may be in the effective state, a collimating unit B in collimating module 1 may be in the invalid state, and a collimating unit C may be in the effective state, then the collimating units A and C may be the collimating units in the first portion, and the collimating unit B may be a collimating unit in the second portion. When the collimating module is further rotated by a certain angle, the collimating unit A may be switched to the effective state, the collimating unit B may be switched to the effective state, and the collimating unit C may be switched to the invalid state, then the collimating units A and B may be the collimating units in the first portion, and the collimating unit C may be a collimating unit in the second portion.

For example, as shown in FIG. 6A, 610 may represent a relative position between the collimating unit and the detecting module of a first configuration of the collimating unit (e.g., a count of the holes in small apertures may be larger than a count the holes in large apertures), at which time the collimating unit 611 of the first portion is in the effective state, and the collimating unit 612 of the second portion may be in an invalid state; 620 may represent a relative position between the collimating unit and the detecting module 623 of a second configuration of the collimating unit (e.g., a count of the holes in large apertures may be larger than a count the holes in small apertures), at which time the collimating unit in the first portion is in the effective state, and the collimating unit in the second portion may be in the invalid state. In some embodiments, the collimating units in 611 may be all in small apertures, and the collimating units in 621 may be all in large apertures.

In some embodiments, projections, along a radial direction of the accommodating space, of any two of the multiple collimating units on a plane where the detector is located may be independent. Independence of the projections may refer to that there is no overlapped space between the projections, along the radial direction of the accommodating space, of any two of the multiple collimating units on the plane where the detector is located.

In some embodiments, the projections, along the radial direction of the accommodating space, of any two of the multiple collimating units on the plane where the detector is located may overlap each other. A detection efficiency of the detector may be improved when the projections of any two of the multiple collimating units on the plane along the radial direction of the accommodating space are overlapped. The overlapped projected images may be separated and reconstructed through an image processing algorithm. The image processing algorithm may refer to a series of preset determination operations configured to process input data (the overlapped projected images herein) to generate a desired output (such as a separated image or a reconstructed image), and the specific image algorithm may include an image optimization technique or a machine learning model, etc.

In some embodiments, the independence of the projections of any two collimating units on the detector may make the radiation rays passing through the two collimating units do not interfere with each other. Alternatively, the projections of any two collimating units along the radial direction on the plane where the detector is located may be non-overlapped. As used herein, the term “projection” of a component (e.g., the collimating unit, the collimating module, the detecting module, the gap between two adjacent detecting modules) may be a region obtained by projecting the shape of the component onto a plane with a beam of light along a reference direction. The shape of the gap between the two adjacent detecting modules may be defined by edges of the two adjacent collimating modules (e.g., a visible ray or a virtual line). The direction of the beam of light may be parallel to the reference direction. For example, the projection of the collimating unit on a plane where the detector is located along the radial direction of the accommodating space may include a region formed by projecting the shape of the collimating unit onto the plane with a beam of light with a direction parallel to the radial direction. In some embodiments, the plane where the detecting module is located may include a plane passing through a geometric center of the detecting module and perpendicular to the radial direction. In some embodiments, the detecting module may be curved-shape, then the plane where the detecting module is located refers to a plane where a cut surface of the detecting module at the geometric center is located. In some embodiments, the plane where the detecting module is located may include the plane defined by the surface of the detecting module.

By setting the projections of any two collimating units of the multiple collimating units on the detector along the radial direction to be independent of each other, measurement accuracy may be improved, signal interference may be reduced, and imaging quality may be improved.

In some embodiments, each of the collimating modules may correspond to one of the detecting modules. In other words, the count or number of the collimating modules may be less than or equal to the count or number of the detecting modules. A radiation ray passing through a collimating unit in the effective state in a collimating module may be irradiated on the detecting module corresponding to the collimating module; and, a radiation ray passing through a collimating unit in the invalid state in the collimating module may be irradiated in a gap between the detecting module and the adjacent detecting module.

Figure 7:
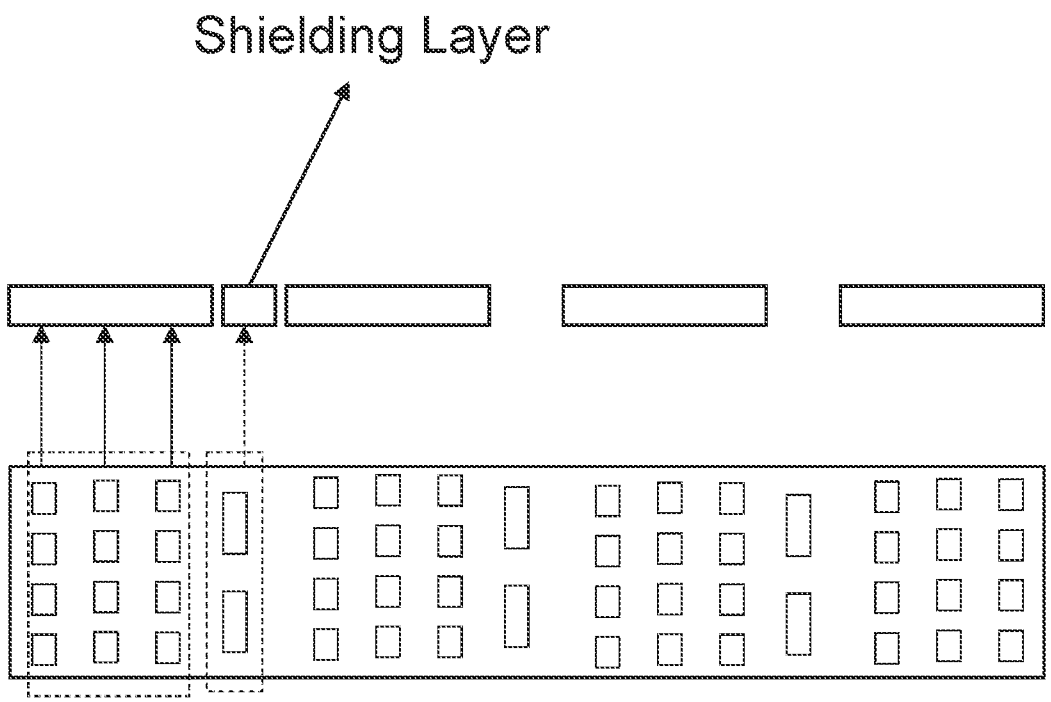
FIG. 7 is a schematic diagram illustrating an exemplary reception of radiation rays according to some embodiments of the present disclosure.

In some embodiments, the gap between two adjacent detecting modules may include a shielding layer. The radiation ray passing through a collimating unit in the invalid state in the collimating module and reaching the gap between two adjacent detecting modules may be absorbed by the shielding layer. As shown in FIG. 7, the radiation rays passing through the collimating unit in the invalid state may further be irradiated on a shielding layer between two adjacent detecting modules. In some embodiments, the shielding layer may be a component made of a dense material (e.g., lead or tungsten, etc.) that has a high attenuation coefficient. In some embodiments, the material of the shielding layer may be the same as the material of the main body of the collimating unit. In some embodiments, the material of the shielding layer may be different from the material of the main body of the collimating unit. It should be noted that the count of detecting modules in FIG. 7 is merely for illustration and not limit the scope of the present disclosure, and a count of detecting modules may be multiple.

In some embodiments, when the first portion of the multiple collimating units in a collimating module is in an edge region of the collimating module and in the effective state, the second portion of the multiple collimating units in the collimating module may be in an middle region of the collimating module and in the invalid state, and the projection of the second portion of the multiple collimating units along a radial direction on the detector may be located within one single gap between the detecting module and the adjacent detecting module.

Figure 6C:
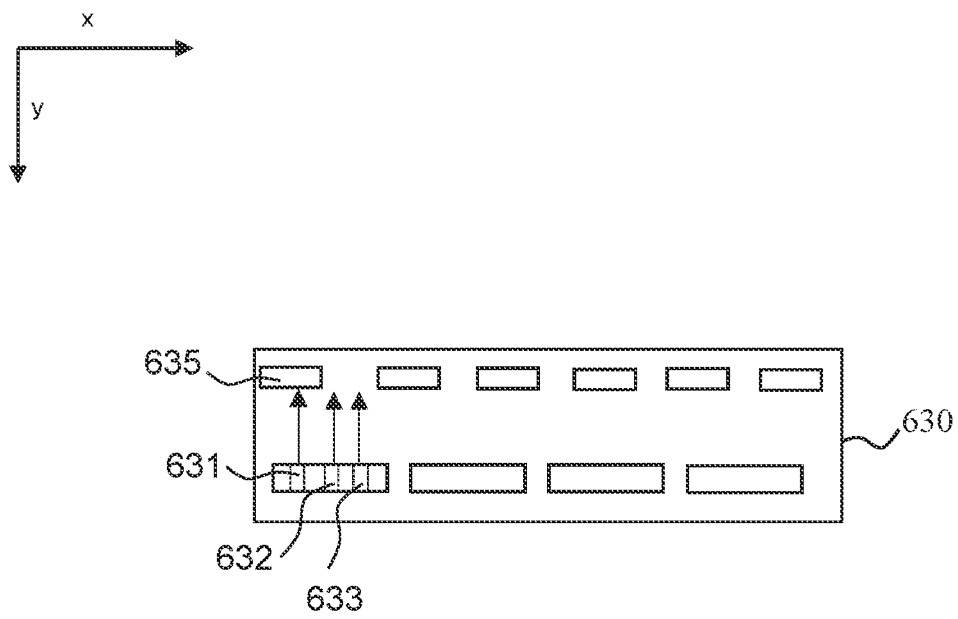
FIG. 6C is a schematic diagram illustrating an exemplary state of collimating units according to some embodiments of the present disclosure.

For example, as shown in FIG. 6C, a collimating module may include a collimating unit 631, a collimating unit 632, and a collimating unit 633. The collimating unit 631 and the collimating unit 633 may be located at the edge regions of the collimating module and the collimating unit 632 may be located at the middle region of the collimating module. When the collimating unit 631 is in the effective state, and the collimating unit 632 and the collimating unit 633 may be in the invalid state, the collimating unit 631 may belong to the first portion, and the collimating unit 632 and the collimating unit 633 may belong to the second portion. A projection of the collimating unit 632 and the collimating unit 633 may be located within one single gap between the detecting module 635 and the adjacent detecting module of the detecting module 635.

In some embodiments, when the first portion of the multiple collimating units is in a middle region of the collimating module and is in the effective state, the second portion of the multiple collimating units may be in two edge regions of the collimating module, the projection of the second portion of the multiple collimating units along the radial direction on the detector may be located within two gaps each of which is between the detecting module and the adjacent detecting module.

Figure 6D:
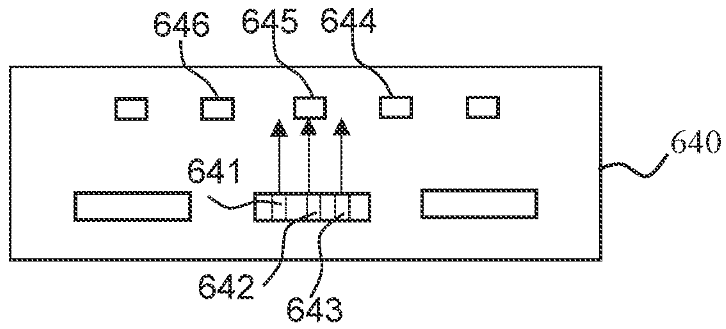
FIG. 6D is a schematic diagram illustrating an exemplary state of collimating units according to some embodiments of the present disclosure.

For example, as shown in FIG. 6D, a collimating module may include a collimating unit 641, a collimating unit 642, and a collimating unit 643. The collimating unit 641 and the collimating unit 643 may be located at the edge regions of the collimating module and the collimating unit 642 may be located at the middle region of the collimating module. When the collimating unit 642 is in the effective state, the collimating unit 641 and the collimating unit 643 may be in the invalid state. The collimating unit 642 may belong to the first portion of the collimating units in the collimating module, and the collimating unit 641 and the collimating unit 643 may belong to the second portion of the collimating units in the collimating module. The projections of the collimating unit 641 and the collimating unit 643 along the radial direction on a plane where the detecting modules are located may be within different gaps. For example, the projection of the collimating unit 641 along the radial direction on the plane where the detector is located may be within the gap between the detecting module 645 and an adjacent detecting module 644. The projection of the collimating unit 643 along the radial direction on the plane where the detector is located may be within the gap between the detecting module 645 and another adjacent detecting module 646. The two adjacent detecting modules 644 and 646 of the detecting module 645 may be located on two sides of the detecting module 645, respectively.

In some embodiments, a projection of a collimating unit in the effective state along a radial direction on the detector may be located within a detecting module.

As used herein, the projection located within the detecting module may refer to a region formed by the projection may be within the region where the detecting module is located.

In some embodiments, when a collimating unit is in the effective state, the collimator may be driven to rotate an angle based on a sampling rate of the imaging system.

A sampling rate of an imaging system may be a spatial frequency where the detector collects data. The sampling rate may reflect the ability of the detector to discriminate different radiation rays in space.

In some embodiments, by driving the collimator to rotate to precisely micro-move a collimation angle, the sampling rate may be increased, and the imaging quality may be improved. For example, the collimator may be driven to rotate a plurality of times by a small magnitude (e.g., half the width of a detector pixel) to collect multi-angle information. A micro-movement of a collimating unit to adjust the collimation angle of the collimating unit may further eliminate a quantization error caused by a detector pixelation. For example, rotating the collimator with half the width of a detector pixel may be equivalent to reducing a half the size of a detector pixel along a rotation direction. The position of the collimating unit in the effective state relative to the detecting module may affect the sampling rate of the detecting module. For example, by driving the collimator to rotate the plurality of times, the positions of the different detecting units in the detecting module may be adjusted relatively to the position of the detector module. The projection of the collimating unit in the effective state along the radial direction towards the plane where the detecting module is located may be located within an edge region or a center region of the detecting module by rotating the collimator around the axial direction. When the projection of the collimating unit in the effective state along the radial direction towards the plane where the detecting module is located may be located within the center region of the detecting module, since the radiation lines passing through the collimating units are received by the detecting module over a relatively large region, the sampling rate of the detecting module may be increased. In some embodiments, the detecting module may include multiple scintillators, each of the multiple scintillators may correspond to a detector pixel, and a desired sampling rate may be satisfied by adjusting a relative position relationship between the holes in the collimating units in the effective state and the multiple scintillators. If the radiation rays passing through the set of holes in a collimating unit in the effective state are detected by each of the multiple scintillators in the detecting module, the sample rate may be high; and if the radiation rays passing through the set of holes in a collimating unit in the effective state are detected by a portion of the multiple scintillators in the detecting module, the sample rate may be low.

In some embodiments, by obtaining a relationship between the sampling rate and an adjustment angle, an adjustment angle at the desired sampling rate may be determined based on the relationship between the sampling rate and an adjustment angle, thereby achieving needs at different sampling rates.

The rotation transmission apparatus 230 may be configured to drive the collimator 220 to rotate. In some embodiments, the rotation transmission apparatus 230 may include a rotating support and a driving component. The multiple collimating modules may be arranged on the rotating support, and the driving component may be configured to drive the rotating support to rotate.

The rotating support may be configured to hold and support the multiple collimating modules in the collimator 220. In some embodiments, the rotating support may be rotatably connected with the gantry of the imaging apparatus 200.

In some embodiments, the rotating support may be made of metal or other robust material. The rotating support may be driven by the driving component to rotate. For example, the rotating support may include a turntable and a collimator supporting structure. The collimator supporting structure may be connected to the turntable, the turntable may be capable of rotating under the driving component, and the collimator supporting structure may be configured to support and fix the collimator to cause the collimator to rotate under the driving of the turntable.

The driving component may be a component configured to drive the rotating support to rotate. In some embodiments, the driving component may include a motor and a transmission element. In some embodiments, the motor may include a stepper motor, a servo motor, or the like, or a combination thereof. The transmission element may include a gear transmission, a belt transmission, or the like, or a combination thereof. The motor may drive the rotating support to rotate through the transmission element. For example, the motor may include a rotation shaft (e.g., a rotor) connected with the transmission element. The motion may drive the rotation shaft to rotate and the rotation of the rotation shaft may drive the rotation of the rotating support to rotate.

In some embodiments, the rotation transmission apparatus 230 may further include a positioning component configured to determine positions of the collimating modules in the collimator 220. A precise position of the collimating module in space may be monitored and determined by the positioning component for obtaining high quality imaging results.

In some embodiments, the positioning component may be implemented through a magnetic scale, an optical encoder, a Hall effect sensor, a voltage-based sensor, or a vision system (e.g., by capturing an image and tracking a position of the collimating module through image processing and algorithmic recognition). For example, the turntable may be equipped with a high-precision positioning component (e.g., a magnetic scale), which may be configured to measure an angle of rotation of the turntable in real time to reach a purpose of precise control.

In some embodiments, the motor and the positioning component may cooperate to cause the collimator to rotate a plurality of times with a small amplitude (e.g., half the width of a detector pixel) to collect information from multiple angles and improve the quality of image reconstruction.

In some embodiments, the motor and the positioning component may be used for calibration of the detector. More descriptions of the calibration of the collimator may be found in the descriptions below.

In some embodiments, a length of the gap between two adjacent detecting modules along the circumference direction may exceed a length of a collimating module along the circumference direction.

Figure 8A:
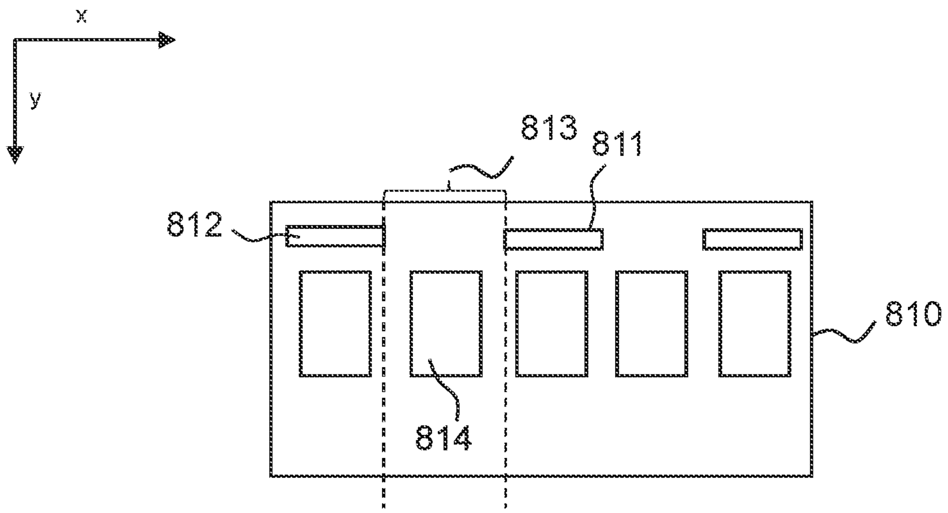
FIG. 8A is an exemplary schematic diagram illustrating a gap between two adjacent detecting modules according to some embodiments of the present disclosure.

For example, FIG. 8A is an exemplary schematic diagram illustrating a gap between two adjacent detecting modules according to some embodiments of the present disclosure. As shown in FIG. 8A, the length 813 of a gap between a detecting module 811 and a detecting module 812 along the circumference direction (x-direction) exceeds a length of the collimating module 814 along the circumference direction. It should be noted that the count of detecting modules in FIG. 8A is merely for illustration and not limit the scope of the present disclosure, and a count of detecting modules may be multiple.

In some embodiments, the length of the gap along the circumference direction may exceed a length of the second portion of the multiple collimating units in the invalid state along the circumference direction.

Figure 8B:
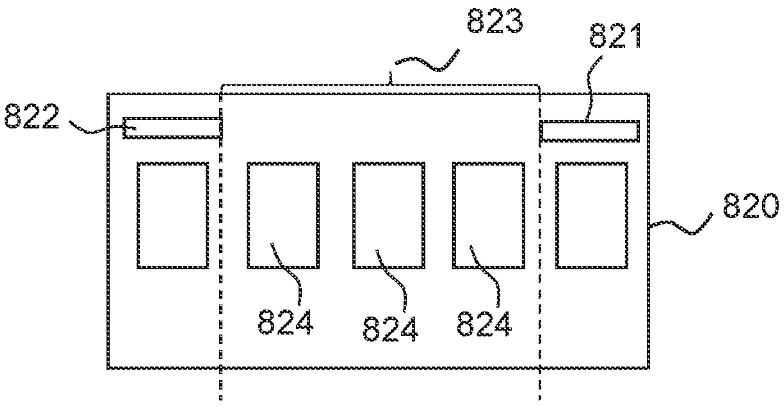
FIG. 8B is an exemplary schematic diagram illustrating a gap between two adjacent detecting modules according to some embodiments of the present disclosure.

For example, FIG. 8B is an exemplary schematic diagram illustrating a gap between two adjacent detecting modules according to some embodiments of the present disclosure. As shown in FIG. 8B, a length 823 of a gap between a detecting module 821 and a detecting module 822 along the circumference direction may exceed a total length of collimating units 824 in the invalid state (e.g., the collimating units of the second portion) along the circumference direction. It should be noted that the count of detecting modules in FIG. 8B is merely for illustration and not limit the scope of the present disclosure, and a count of detecting modules may be multiple.

In some embodiments, the collimator 220 may be provided with a notch 240. The length of the notch 240 of the collimator 220 along the circumference direction may be greater than the length of a collimating module along the circumference direction. The position of the notch 240 may correspond to a detecting module in the detector 210. Radiation rays may pass through the notch and be received by the detecting module corresponding to the notch 240 of the collimator 220. For example, the count or number of the collimating modules in the collimator 220 may be less than the count or number of the detecting modules in the detector 210, such that the notch 240 may be formed between two adjacent collimating modules. In some embodiments, the length of a detecting module may be the same as or similar to the length of a collimating module along the circumference direction, and when the count or number of the collimating modules in the collimator 220 is less than the count or number of the detecting modules in the detector 210 and the length of a gap between two adjacent collimating modules is same as or less than the gap between adjacent detecting modules, the notch 240 of the collimator 220 may be formed.

In some embodiments, a projection of the notch along a radial direction may cover a detecting module, such that radiation rays passing through the notch may be irradiated on the detecting module.

Therefore, it is possible to not provide the collimating module in a certain region of the collimator 220 along the circumference direction so that the radiation rays passing through the notch of the collimator 220 may be irradiated to the detecting module without passing through the collimating module, and this region of the collimator 220 where the collimating module is not arranged may be the notch of the collimator 220.

As shown in FIG. 2, there is no collimating module arranged at the notch 240 when the collimating modules are arranged along the circumference direction. It should be noted that the detecting module corresponding to the notch 240 may be omitted from FIG. 2 here for the purpose of illustrating a structure of the notch 240. A projection of the notch 240 on a plane, e.g., the plane where the detector is located along a radial direction of the accommodating space may occupy a region of the plane. A projection of a detecting module on the plane, e.g., the plane where the detector is located may occupy a region of the plane. When the position of the detecting module corresponds to the position of the notch, the region occupied by the projection of the notch 240 may be located within the region occupied by the projection of the detecting module. The length of the notch 240 along the circumference direction may be less than or equal to the length of each detecting module in the detector 210 along the circumference direction.

Accordingly, all of the radiation rays passing through the notch 240 may be received by the detecting module when the position of the detecting module corresponds to the position of the notch 240.

In some embodiments, the notch 240 may be used for calibration of each of the detecting modules by rotating the collimator to cause the projection of the notch 240 along the radial direction on the detector to cover each of the detecting modules.

Along the rotation of the collimator 220, the position of the notch 240 may correspond to the position of one of the multiple detecting modules of the detector 210. In other words, radiation rays passing through the notch 240 may be detected by the detector module corresponding to the position of the notch 240. Then the projection data may be generated by the detecting module in response to detecting the radiation rays passing through the notch 240. The detecting module may be calibrated based on the projection data generated by the detecting module. Accordingly, the notch 240 may be rotated along the rotation of the collimator 220 to a position corresponding to each of the multiple detecting modules of the detector 210. Further, each of the multiple detecting modules of the detector 210 may be calibrated based on projection data generated by each of the multiple detecting modules of the detector 210, so that the calibration of a whole-ring detector may be implemented more simply and accurately after one rotation of the collimator.

In some embodiments, the processor 140 may cause the collimator 220 to rotate around the axis of the imaging apparatus to cause a target collimating unit of the multiple collimating units in each collimating module of the collimator 220 to be in an effective state. Then one or more images of the subject may be reconstructed based on the scan data of the subject. In some embodiments, the processor 140 may determine the target collimating unit in each collimating module of the collimator 220 that needs to be in the effective state according to imaging requirements on one or more imaging parameters. For example, if the subject includes the heart of the human body, the target collimating unit may correspond to an FOV whose center is misalign with a center of a circumference plane where the target collimating unit is located. As another example, if the subject includes the body of a patient, the target collimating unit may correspond to a maximum FOV. In some embodiments, the processor 140 may rotate the collimator 220 with a rotation angle to cause the target collimating unit in the effective state. The rotation angle may be determined based on a position of the target collimating unit is located. The position of the target collimating unit may be determined based on a positioning component.

In some embodiments, the processor 140 may cause the collimator 220 to rotate around the axis of the imaging apparatus such that the notch 240 of the collimator corresponding to a position of a target detecting module. The processor 140 may cause the imaging apparatus to scan a second subject (e.g., a phantom) to obtain scan data of the second subject. At least a portion of the scan data may be generated by the target detecting module. The processor 140 may calibrate the target detecting module based on the scan data of the second subject.

For example, after arranging the parameters of the imaging apparatus, a radioactive source may be placed in the detecting region (e.g., within the accommodation space), and then data acquisition may be performed to obtain projection data acquired by the detecting module corresponding to the notch 240, and the detecting module may be calibrated based on the projection data using a calibration algorithm (e.g., a homogeneity calibration algorithm, an energy calibration algorithm, etc.)

In some embodiments, collimating units in the multiple collimating modules of the collimator 220 may be in the effective state simultaneously. The collimating units in the multiple collimating modules that are in the effective state simultaneously may be in the same configuration.

The configuration of the collimating units in the multiple collimating modules that are in the effective state simultaneously may be related to an imaging requirement. The image requirement may be defined by one or more imaging parameters such as the field of view (FOV), a system sensitivity, a spatial resolution, a detecting rate, etc., of the imaging apparatus 200. Accordingly, the configuration of each collimating unit in a collimating module may be designed according to an imaging requirement. For example, the sensitivity may be determined based on the aperture of the hole and a distance between the collimator and a subject to be scanned. As another example, the resolution may be determined based on the aperture of the hole and the opening angle.

As a further, a field of view corresponding to a relatively large aperture may be larger than the field of view of a smaller aperture because the large aperture allows more rays to pass through and may form a wide field of view. At the same time, the more radiation rays passing through the larger aperture to reach the detector, the more sensitivity may be improved; while the small aperture may precisely limit a range of path of the radiation rays that pass through the collimator, which may improve the spatial resolution.

Figure 9:
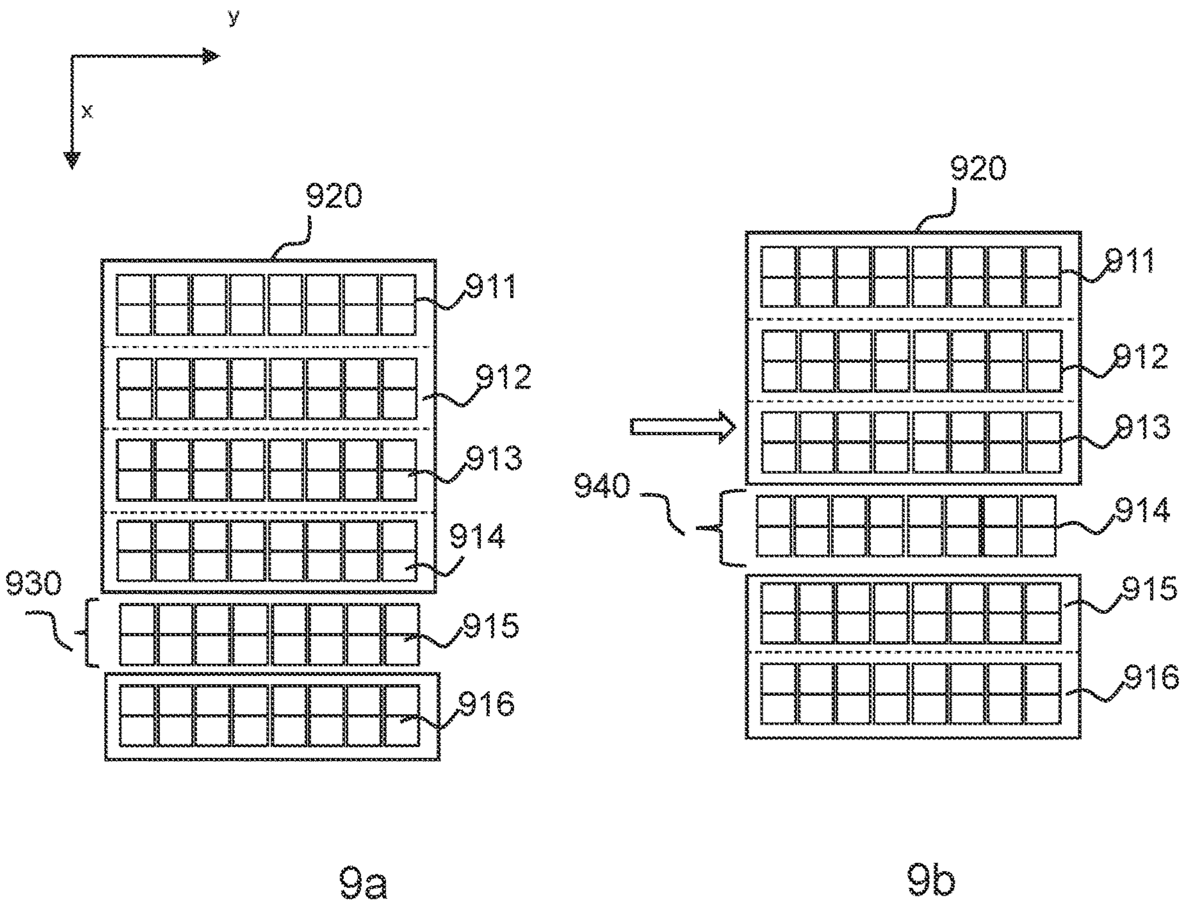
FIG. 9 is a schematic diagram illustrating an exemplary notch of a collimating unit according to some embodiments of the present disclosure.

FIG. 9 is a schematic diagram illustrating an exemplary notch of a collimator in an overlook view according to some embodiments of the present disclosure. As shown in FIG. 9, 9*a* represents a position relationship between the detecting modules and the collimating modules at a first moment, 911, 912, 913, 914, 915 and 916 represents the detecting modules, 920 represents the collimating modules, and 930 represents a position of the notch of the collimator at the first moment. The notch of the collimator may correspond to a detecting module 915 and the first moment. When the collimating modules 920 are driven to rotate, the notch of the collimator may reach a position of 940 at a second moment. The notch may correspond to the detecting module 914 at the second moment. It should be noted that the count of detecting modules in FIG. 9 is merely for illustration and not limit the scope of the present disclosure, and a count of detecting modules may be multiple.

In some embodiments, the multiple collimating units may include a first collimating unit (e.g., a pinhole collimating unit) and a second collimating unit (e.g., a pinhole collimating unit), the first collimating unit may correspond to a first field of view (FOV), the second collimating unit may correspond to a second FOV that is different from the first FOV.

Figure 10A:
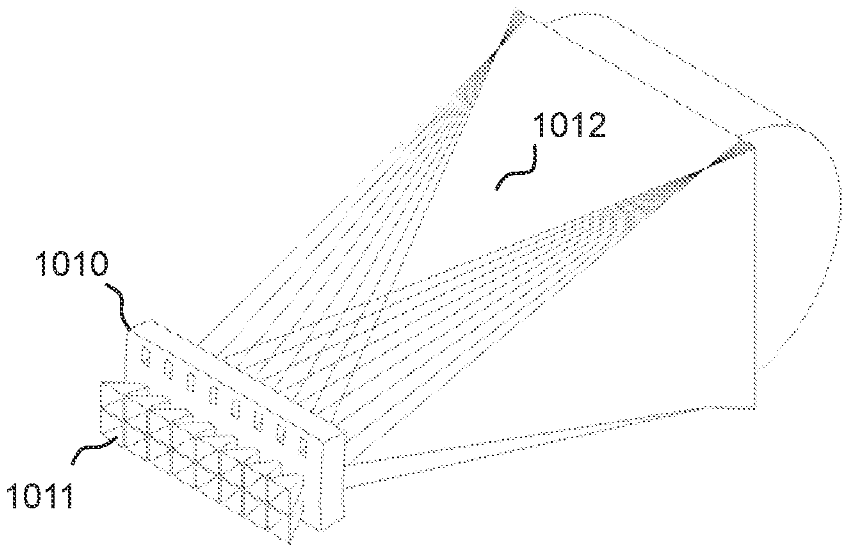
FIG. 10A is a schematic diagram illustrating an exemplary field of view of a collimating unit according to some embodiments of the present disclosure.
Figure 10B:
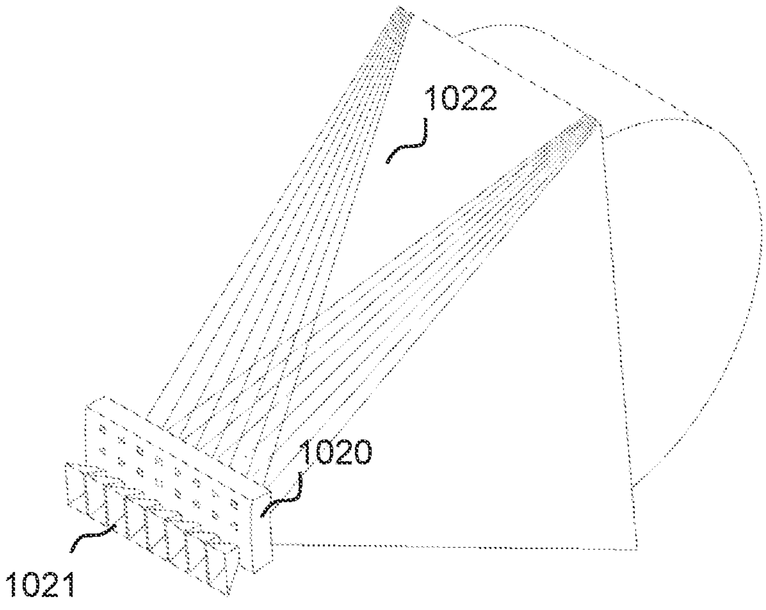
FIG. 10B is a schematic diagram illustrating an exemplary field of view of a collimating unit according to some embodiments of the present disclosure.

In some embodiments, different fields of view may be obtained by configuring different rows (count of holes arranged along the circumference direction) of holes in the collimating unit. For example, FIGS. 10A and 10B are schematic diagrams illustrating an exemplary field of view of a collimating module according to some embodiments of the present disclosure. As shown in FIG. 10A and FIG. 10B, the collimating module includes a collimating unit 1010 and a collimating unit 1020. A double row of holes may be provided in the collimating unit 1010 corresponding to a first FOV 1012 (e.g., narrow field of view) and a single row of holes may be provided in the collimating unit 1020 corresponding to a second FOV 1022. The double row of holes of the collimating unit 1010 may correspond to incident radiation rays 1011 in FIG. 10A, and the incident radiation rays 1011 may characterize a range of incident radiation rays that pass through the double row of holes. The single row of holes of the collimating unit 1020 may correspond to incident radiation rays 1021 in FIG. 10B, and the incident radiation rays 1021 may characterize a range of incident radiation rays that pass through the single row of holes. The opening angle of each of the set of holes of the collimating unit 1010 may be smaller than the opening angle of each of the set of holes of the collimating unit 1020, such that the second FOV of the collimating unit 1020 may be larger than the first FOV of the collimating unit 1010. As shown in FIG. 10A, when the collimating unit 1010 is in the effective state, a range of incident radiation rays 1011 that pass through the double row of holes may be collimated by the double row of holes and a smaller first FOV 1012 may be formed. As shown in FIG. 10B, when the collimating unit 1020 is in the effective state, a range of incident radiation rays 1021 that pass through the single row of holes may be collimated by the single row of holes and a larger second FOV 1022 may be formed. It should be noted that the count of detecting modules in FIG. 10A and FIG. 10B is merely for illustration and not limit the scope of the present disclosure, and a count of detecting modules may be multiple.

It should be noted that the size of the field of view may be mainly related to the opening angle of the hole in the collimating unit, a size of the aperture of the hole in the collimating unit and the area of the detector. For exemplary purposes, a comparison between the narrow field of view and the wide field of view in the above example is shown in FIG. 10A and FIG. 10B, and although the first FOV 1012 corresponding to the double row of holes 1011 in FIG. 10A is smaller than the second FOV 1022 corresponding to the single row of holes 1012, a higher detection efficiency may be obtained.

In some embodiments, the multiple collimating units may include at least one of the first collimating unit or the second collimating unit, and a third collimating unit (e.g., a pinhole collimating unit) may correspond to a third FOV, and a center of the third FOV may be misalign with a center of a circumference plane where the third pinhole collimating unit is located (e.g., the center of the accommodating space or the isocenter of the imaging apparatus).

The center of the third FOV may misalign with the center of the circumference plane where the third collimating unit is located may also be referred to as an eccentric field of view (not shown in the figure). The eccentric field of view may cause the collimator to detect regions that are not located within the center of the axis of rotation but are still located within the effective detecting range.

In some embodiments of the present disclosure, a collimating module including multiple sets of holes in different configurations whose operation state (e.g., the effective state or the invalid state) is switched along the rotation of the collimator around the axis of the accommodating space is provided. Accordingly, using the same imaging apparatus, different imaging requirements may be satisfied by switching the collimating units in different configurations. For example, 1) a collimating module having a wide field of view may be directed at the abdomen, thorax, etc.; 2) a collimating module having a narrow field of view may be configured to be directed at the brain and other specific small-volume organs, and obtain higher sensitivity and resolution; 3) an eccentric field of view collimating module may be directed at the heart and other scanning objects that are not located at an aperture center, and may obtain the higher sensitivity and resolution by fully using an effective detecting area of the detector.

Each set of collimating modules of the holes may be switched by a rotation transmission apparatus so that when a portion of the holes are in operation, the remaining portion of the small apertures may be located within the interval and shielding between the adjacent detecting modules without interfering with current imaging. A rotation angle of the collimating module may also be finely adjusted to increase the sampling rate and enhance the image quality. The imaging system provided in the embodiments of the present disclosure may realize an online switching of the field of view without replacing the collimator, which greatly enhances a convenience of using the imaging system in different scenarios and facilitates an acquisition of high-quality images of different scanning objects.

It should be understood that the system and its modules may be implemented by using various approaches. For example, in some embodiments, the system and its modules may be implemented by hardware, software, or a combination of software and hardware.

It should be noted that the above description of the imaging system and its modules are merely provided for the purpose of descriptive convenience and are not intended to limit the present disclosure to the scope of the cited embodiments. It is understood that for those skilled in the art, after understanding the principle of the system, it may be possible to arbitrarily combine individual modules or form subsystems to connect with other modules without deviating from this principle. In some embodiments, the detecting modules and collimating modules disclosed in FIG. 1 may be different modules in a single system, or a single module may implement the functions of two or more of the above modules. For example, the individual modules may share a storage module, and the individual modules may each have their own storage module. Such variations are within the scope of protection of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Furthermore, the recited order of processing elements or sequences, or the use of numbers, letters, or other designations thereof, are not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may further be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the count of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Therefore, by way of example, but not of limitation, alternative configurations of the embodiments of the application may be utilized in accordance with the teachings herein. Accordingly, embodiments of the present application are not limited to that precisely as shown and described.

What is claimed is:

1. A single-photon emission computed tomography (SPECT) imaging system comprising:

a detector including detecting modules arranged along a circumference direction of an imaging apparatus and configured to form an accommodation space; and a collimator configured to collimate radiation rays emitted from a subject reaching the detector, the collimator including collimating modules arranged along the circumference direction and configured to rotate around an axis of the accommodation space that is perpendicular to the circumference direction;

wherein one of the collimating modules includes multiple collimating units in different configurations, the multiple collimating units are arranged along the circumference direction, each of the multiple collimating units is switched between an effective state and an invalid state via a rotation of the collimator around the axis of the accommodation space;

the collimator includes a notch between two of the collimating modules which are adjacent to one another, a distance between the two of the collimating modules which are adjacent to one another is greater than a length of one of the detecting modules along the circumference direction, a projection of the notch along a radial direction covers the one detecting module, such that radiation rays passing through the notch are irradiated on the one detecting module.

2. The SPECT imaging system of claim 1, wherein the multiple collimating units include a first portion and a second portion, and when the first portion of the multiple collimating units is in the effective state, the second portion of the multiple collimating units is in the invalid state.

3. The SPECT imaging system of claim 2, wherein in the effective state, a projection of the first portion of the multiple collimating units along a radial direction on the detector is located within a detecting module corresponding to the collimating module, and in the invalid state, a projection of the second portion of the multiple collimating units along the radial direction on the detector is located within one or more gaps each of which is between two adjacent detecting modules.

4. The SPECT imaging system of claim 2, wherein each of the collimating modules corresponds to a detecting module among the detecting modules, in the effective state, a radiation ray passing through the first portion of the multiple collimating units is irradiated on the detecting module corresponding to the collimating module, in the invalid state, a radiation ray passing through one collimating unit of the second portion of the multiple collimating units is irradiated in one of the one or more gaps each of which is between the detecting module corresponding to the collimating module and an adjacent detecting module.

5. The SPECT imaging system of claim 2, wherein a gap exists between adjacent detecting modules among the detecting modules, a length of the gap along the circumference direction exceeds a length of the second portion of the multiple collimating units along the circumference direction.

6. The SPECT imaging system of claim 2, wherein when the first portion of the multiple collimating units is in an edge region of the collimating module and in the effective state, the projection of the second portion of the multiple collimating units along a radial direction on the detector is located within one single gap between a detecting module among the detecting modules corresponding to the collimating module and an adjacent detecting module.

7. The SPECT imaging system of claim 2, wherein when the first portion of the multiple collimating units is in a middle region of the collimating module and in the effective state, the second portion of the multiple collimating units is in two edges region of the collimating module, the projection of the second portion of the multiple collimating units along the radial direction on the detector is located within two gaps each of which is between a detecting module corresponding to the collimating module and an adjacent detecting module.

8. The SPECT imaging system of claim 1, wherein a projection, along a radial direction, of each of any two of the multiple collimating units on the detector is independent.

9. The SPECT imaging system of claim 1, wherein a gap exists between adjacent detecting modules among the detecting modules, a length of the gap along the circumference direction exceeds a length of a collimating module along the circumference direction.

10. The SPECT imaging system of claim 1, wherein the notch is used for calibration of each of the detecting modules by rotating the collimator to cause the projection of the notch along the radial direction to cover each of the detecting modules.

11. The SPECT imaging system of claim 1, wherein when one of the multiple collimating units is in the effective state, the collimator is driven to rotate an angle based on a sampling rate of the imaging system.

12. The SPECT imaging system of claim 1, wherein the imaging system further includes a rotation transmission apparatus configured to drive the collimator to rotate, the rotation transmission apparatus including a rotating support and a driving component, the collimating modules are arranged on the rotating support, and the driving component is configured to drive the rotating support to rotate.

13. The SPECT imaging system of claim 12, wherein the rotation transmission apparatus further includes a positioning component configured to determine positions of the collimating modules.

14. The SPECT imaging system of claim 1, wherein a configuration of the one of the multiple collimating units is defined by one or more structure parameters including at least one of an aperture of a hole in the one of the multiple collimating units, a length of the hole, a taper angle of the hole, each of the multiple collimating units corresponds to one imaging requirement on one or more imaging parameters.

15. The SPECT imaging system of claim 1, wherein the multiple collimating units include a first collimating unit and a second collimating unit, the first collimating unit corresponds to a first field of view (FOV), and the second collimating unit corresponds to a second FOV that is different from the first FOV.

16. The SPECT imaging system of claim 15, wherein the multiple collimating units include a third collimating unit corresponding to a third FOV, and a center of the third FOV is misaligned with a center of a circumference plane where the third collimating unit is located.

* * * * *